(12) United States Patent
Old et al.

(10) Patent No.: US 8,039,496 B2
(45) Date of Patent: *Oct. 18, 2011

(54) THERAPEUTIC COMPOUNDS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/523,409

(22) PCT Filed: Jan. 22, 2008

(86) PCT No.: PCT/US2008/051650
§ 371 (c)(1),
(2), (4) Date: Jul. 16, 2009

(87) PCT Pub. No.: WO2008/091860
PCT Pub. Date: Jul. 31, 2008

(65) Prior Publication Data
US 2010/0029735 A1 Feb. 4, 2010

Related U.S. Application Data

(60) Provisional application No. 60/886,013, filed on Jan. 22, 2007.

(51) Int. Cl.
| | |
|---|---|
| A61K 31/381 | (2006.01) |
| A61K 31/41 | (2006.01) |
| C07D 257/04 | (2006.01) |
| C07D 333/22 | (2006.01) |
| C07D 333/26 | (2006.01) |
| C07D 333/34 | (2006.01) |

(52) U.S. Cl. ........ 514/382; 514/445; 514/448; 548/252; 549/70; 549/71; 549/6; 549/62

(58) Field of Classification Search .......... None
See application file for complete search history.

(56) References Cited

U.S. PATENT DOCUMENTS

| | | | | |
|---|---|---|---|---|
| 6,710,072 | B2 * | 3/2004 | Burk et al. | 514/438 |
| 7,091,231 | B2 | 8/2006 | Donde | |
| 7,507,817 | B2 * | 3/2009 | Old et al. | 544/106 |
| 2009/0270385 | A1 * | 10/2009 | Old et al. | 514/231.5 |
| 2009/0270386 | A1 * | 10/2009 | Old et al. | 514/231.5 |

OTHER PUBLICATIONS

Horig et al. Journal of Translational Medicine, 2:44 (2004).*
Schafer et al. Drug Discovery Today, 13:913 (2008).*
Han et. al. (Biorganic & Medicinal Chemistry Letters 15 (2005) 3487-3490).
Orlek et al. (J. Med. Chem. 1991, 34, 2726-2735).
Anderson et al. (Eur. J. Med. Chem. 1996, 31, 417-425).
Kohara et al. (J. Med. Chem. 1996, 39, 5228-5235).
Drysdale et al. (J. Med. Chem. 1992, 35, 2573-2581).
U.S. Appl. No. 60/757,696, filed Jan. 10, 2006, David W. Old, et al.
U.S. Appl. No. 60/805,285, filed Jun. 20, 2006, David W. Old, et al.
U.S. Appl. No. 11/553,143, filed Oct. 26, 2006, Yariv Donde.

* cited by examiner

Primary Examiner — Yong Chu
Assistant Examiner — Michael Barker
(74) Attorney, Agent, or Firm — Kevin J. Forrestal; John E. Wurst; Allergen, Inc.

(57) ABSTRACT

Disclosed herein is a compound of the formula. Therapeutic methods, compositions, and medicaments for the treatment of glaucoma or ocular hypertension related thereto are also disclosed.

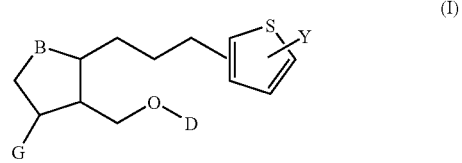

(I)

16 Claims, No Drawings

THERAPEUTIC COMPOUNDS

CROSS REFERENCE TO RELATED APPLICATIONS

This is a national stage application under 35 U.S.C. §371 of PCT patent application PCT/US2008/51650, filed on Jan. 22, 2008, which claims the benefit of U.S. Provisional Patent Application 60/886,013, filed Jan. 22, 2007, each of which is hereby incorporated by reference in its entirety.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

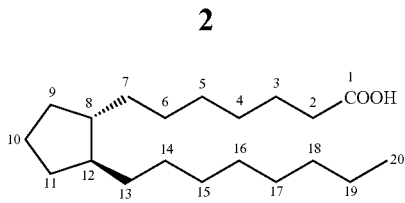

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound of the formula

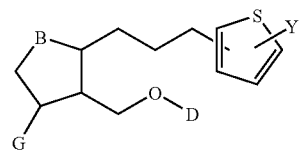

or a pharmaceutically acceptable salt or a prodrug thereof;
wherein Y is an organic acid functional group, or an amide or ester thereof comprising up to 12 carbon atoms; or Y is
hydroxymethyl or an ether thereof comprising up to 12 carbon atoms; or Y is a tetrazolyl functional group;
B is C=O, $CH_2$, CHOH, CHCl, CHF, CHBr, or CHCN;
G is OH or H; and
D is substituted phenyl.

These compounds have several chiral centers. While all stereoisomers are contemplated herein, those shown below are believed to be particularly useful.

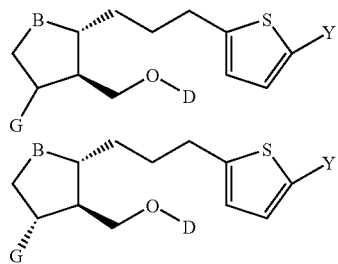

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated for Y. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

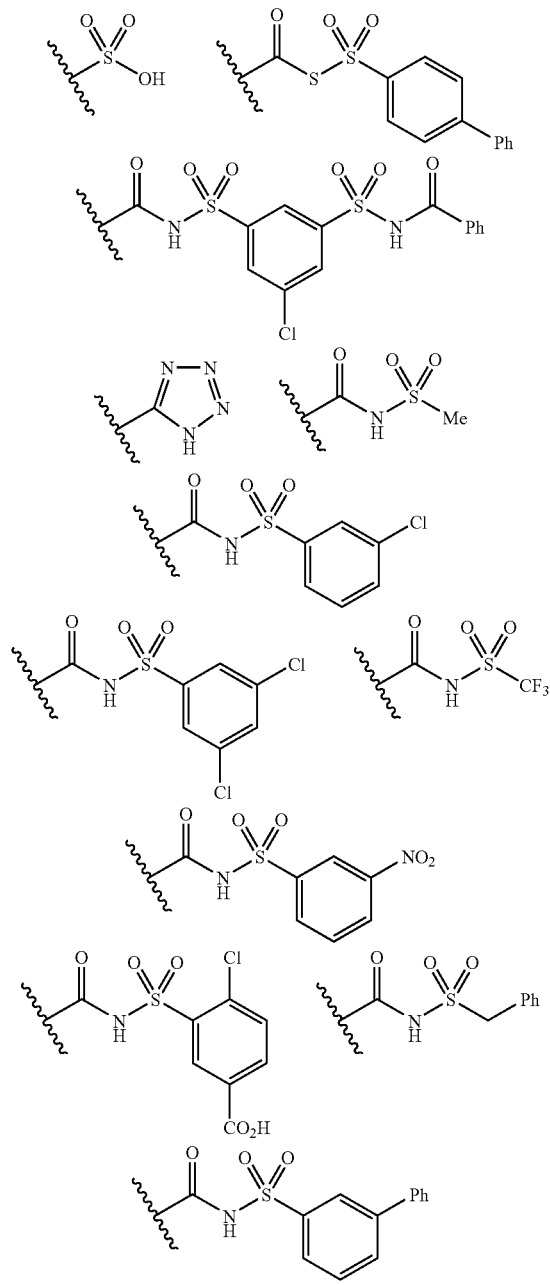

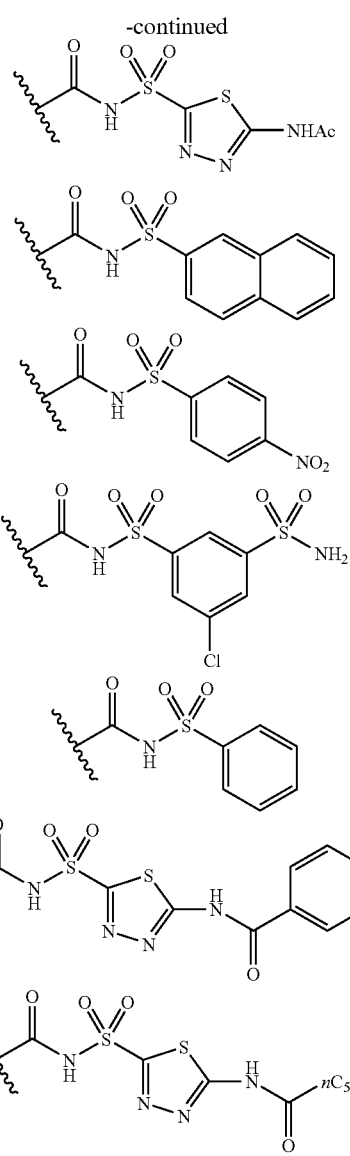

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 3, 9, 10, 11, 12, 13, or 14 carbon atoms.

Finally, while not intending to limit the scope of the invention in any way, Y may be a tetrazolyl functional group.

Thus, while not intending to be limiting, the structures below exemplify what is meant by tetrazolyl; carboxylic acid, phosphonic acid, sulfonic acid, and their esters and amides; hydroxymethyl and ether of hydroxymethyl. In these structures, R is H or hydrocarbyl, subject to the constraints defined herein.

Each structure below represents a specific embodiment which is individually contemplated, as well as pharmaceutically acceptable salts and prodrugs of compounds which are represented by the structures.

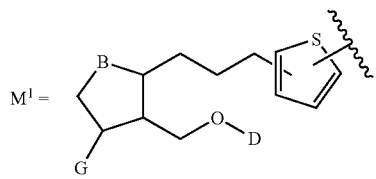

| Organic Acids | Esters | Amides |
|---|---|---|
| $M^1$—$CO_2H$  Carboxylic Acid | $M^1$—$CO_2R$  Carboxylic Acid Ester | $M^1$—$CO_2NR_2$  Carboxylic Acid Amide |
| $M^1$—$P(O)(OH)_2$  Phosphonic Acid | $M^1$—$P(O)(OH)OR$  Phosphonic Acid Ester | $M^1$—$P(O)(OH)NR_2$  Phosphonic Acid Amide |
| $M^1$—$SO_3H$  Sulfonic Acid | $M^1$—$SO_3R$  Sulfonic Acid Ester | $M^1$—$SO_3NR_2$  Sulfonic Acid Amide |
| $M^1$—$CH_2OH$  Hydroxymethyl | $M^1$—$CH_2OR$  Ether | Tetrazolyl |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

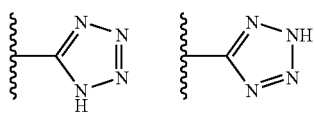

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

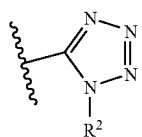

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

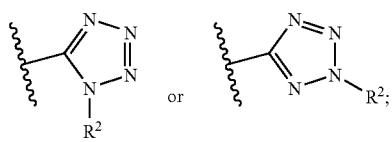

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

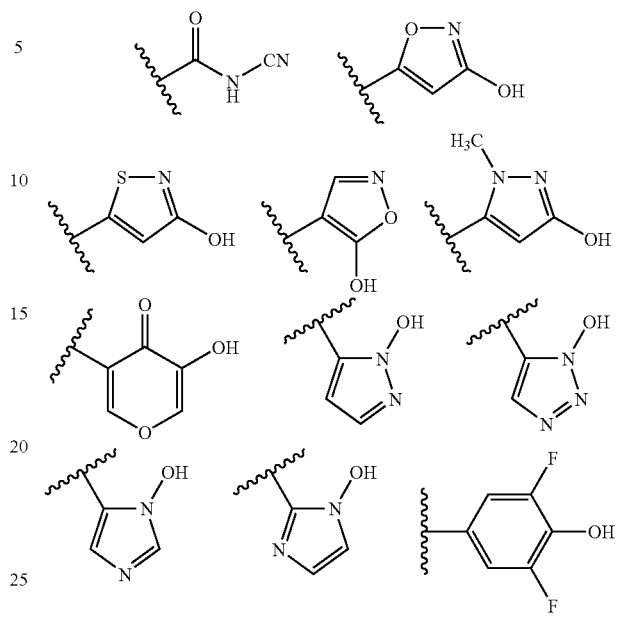

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

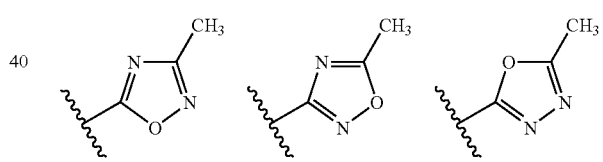

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

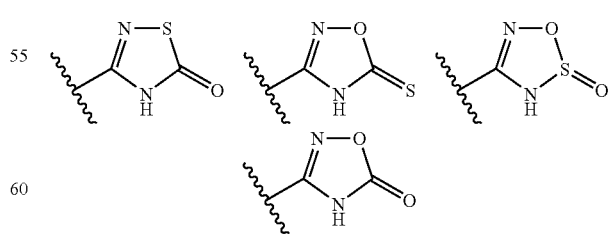

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

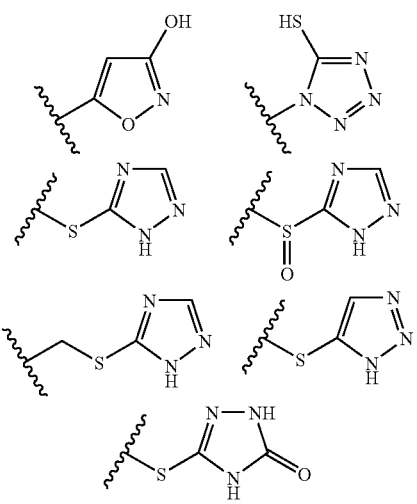

As used herein, substituted phenyl refers to phenyl having one or more substituents. The substituents of phenyl have from 0 to 6 carbon atoms, from 0 to 3 atoms independently selected from O, S, N, F, Cl, Br, or I, and from 0 to 15 hydrogen atoms. If a substituent is a salt, such as a carboxylic acid, and it is associated with a counterion, the counterion is not counted as an atom of the substituent. For example, $CO_2$—$Na^+$ is treated as having 1 carbon and 2 oxygen atoms. Substituents must be sufficiently stable to be stored in a bottle at room temperature under a normal atmosphere for at least 12 hours, or stable enough to be useful for any purpose disclosed herein. Examples of substituents include, but are not limited to:

hydrocarbyl, including alkyl, alkenyl, alkynyl, which are linear, branched, or cyclic, such as methyl, ethyl, propyl isomers, butyl isomers, and the like;

hydrocarbyloxy, including alkoxy, alkenoxy, alkynoxy; such as —$OCH_3$, OEthyl, O-iPropyl; and the like;

acyl, i.e.

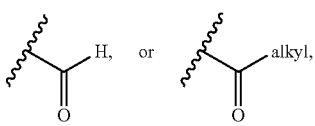

including acetyl, propanyl, and the like;

acyloxy, i.e. —O-acyl, including formate, acetate, propanoate, and the like;

amino, i.e. $NH_2$, NH(hydrocarbyl), or N(hydrocarbyl)$_2$;

hydroxylalkyl, meaning alkyl having one or more hydroxyl groups, such as $CH_2OH$, $CH_2CH_2OH$, and the like;

$CF_3$;
F;
Cl;
Br;
I;
CN;
$NO_2$;
$SO_3H$, and/or
OH.

Substituents on phenyl may be the same or different.
In one embodiment, phenyl has 1, 2, or 3 substituents.

In another embodiment, at least one substituent is $C_{1-3}$ alkyl, Cl, or F.

In another embodiment, all substituents are $C_{1-3}$ alkyl, Cl, F, or hydroxyalkyl.

Compounds of the following structures are specifically contemplated as individual embodiments.

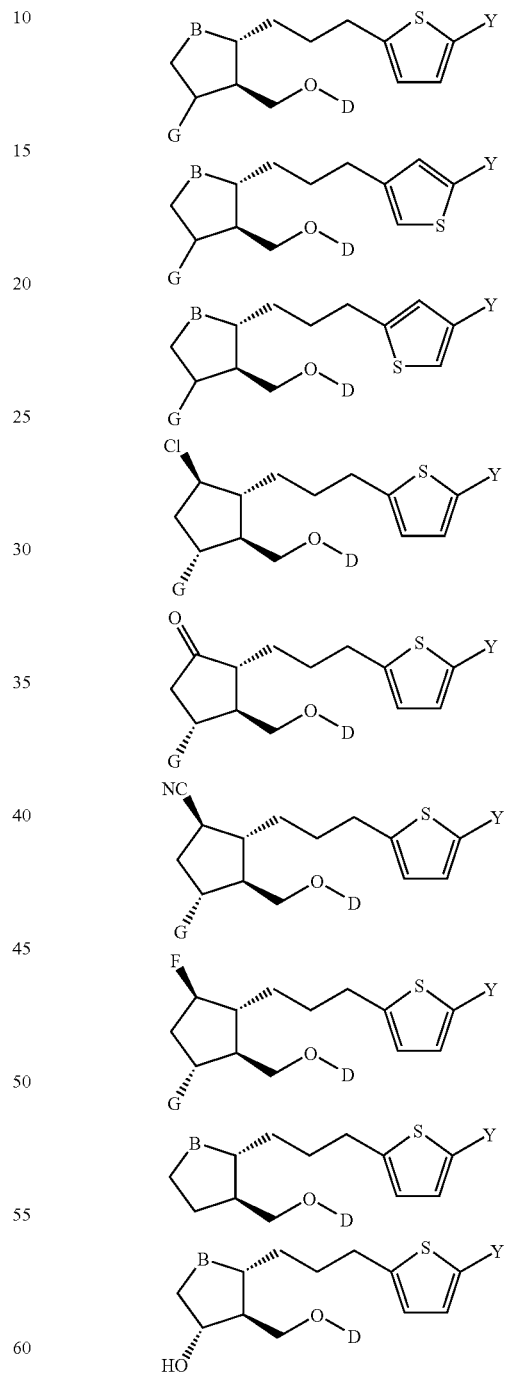

These compounds are useful for treating glaucoma and elevated intraocular pressure.

For the purposes of this disclosure, "treat," "treating," or "treatment" refer to the use of a compound, composition, therapeutically active agent, or drug in the diagnosis, cure, mitigation, treatment, prevention of disease or other undesirable condition.

Synthetic Methods

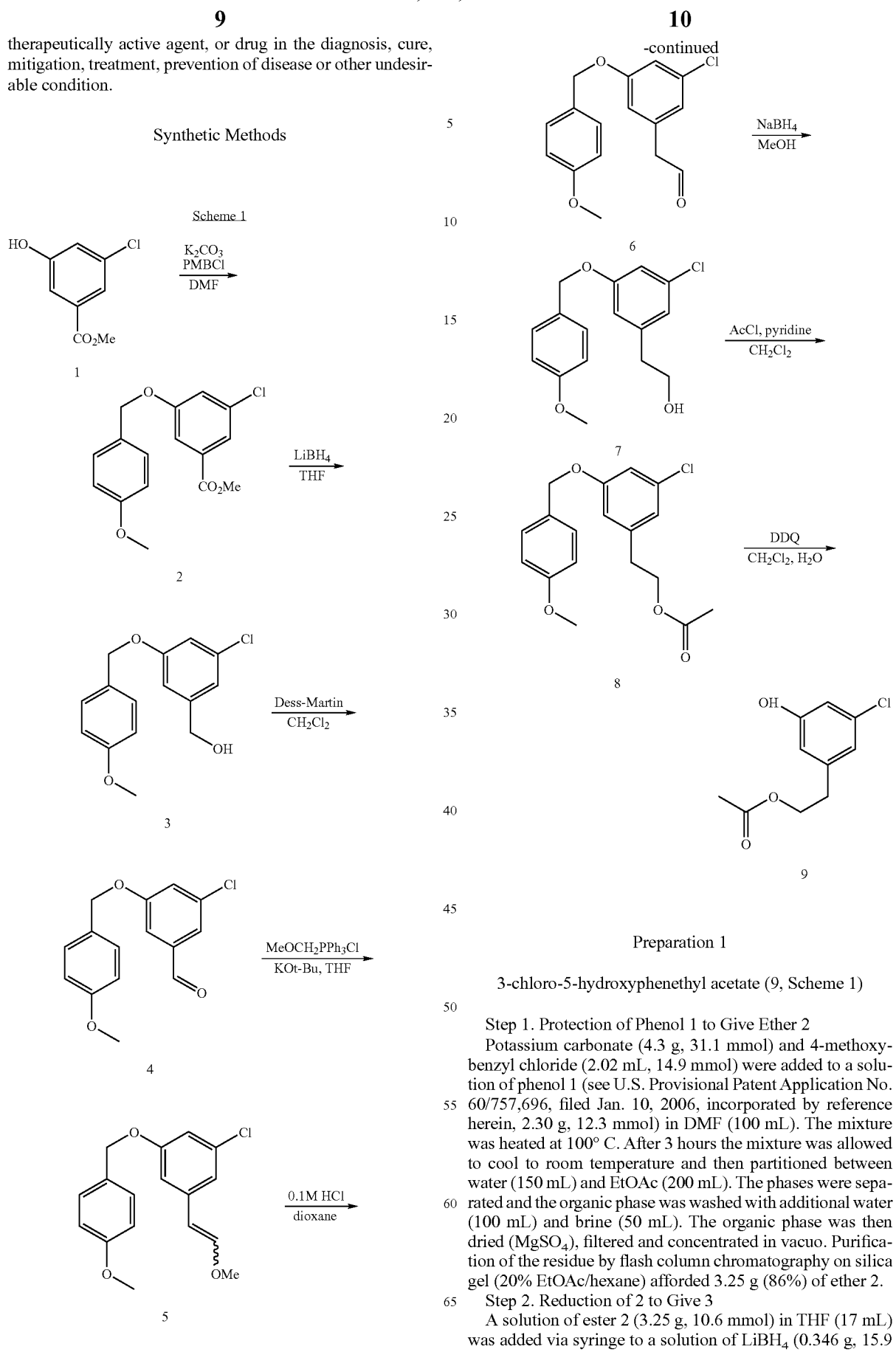

Preparation 1

3-chloro-5-hydroxyphenethyl acetate (9, Scheme 1)

Step 1. Protection of Phenol 1 to Give Ether 2

Potassium carbonate (4.3 g, 31.1 mmol) and 4-methoxybenzyl chloride (2.02 mL, 14.9 mmol) were added to a solution of phenol 1 (see U.S. Provisional Patent Application No. 60/757,696, filed Jan. 10, 2006, incorporated by reference herein, 2.30 g, 12.3 mmol) in DMF (100 mL). The mixture was heated at 100° C. After 3 hours the mixture was allowed to cool to room temperature and then partitioned between water (150 mL) and EtOAc (200 mL). The phases were separated and the organic phase was washed with additional water (100 mL) and brine (50 mL). The organic phase was then dried (MgSO$_4$), filtered and concentrated in vacuo. Purification of the residue by flash column chromatography on silica gel (20% EtOAc/hexane) afforded 3.25 g (86%) of ether 2.

Step 2. Reduction of 2 to Give 3

A solution of ester 2 (3.25 g, 10.6 mmol) in THF (17 mL) was added via syringe to a solution of LiBH$_4$ (0.346 g, 15.9 mmol) in THF (5 mL) at 0° C. The mixture was heated at 80° C. overnight. The reaction mixture was allowed to cool to room temperature, quenched with water, diluted with 5% aqueous citric acid (100 mL) and extracted with EtOAc (75 mL). The organic phase was dried (MgSO$_4$), filtered and concentrated in vacuo. Purification of the crude residue by flash column chromatography on silica gel (30% EtOAc/hexane) afforded 2.91 g (99%) of alcohol 3.

Step 3. Oxidation of 3 to Give 4

A solution of alcohol 3 (2.50 g, 8.97 mmol) in CH$_2$Cl$_2$ (125 mL) was added to a solution of Dess-Martin periodinane (4.57 g, 10.8 mmol) in CH$_2$Cl$_2$ (125 mL). After 2 hours at room temperature the reaction was partitioned between water (500 mL) and CH$_2$Cl$_2$ (300 mL). The phases were separated and the aqueous phase was extracted with CH$_2$Cl$_2$ (2×250 mL). The combined organic phase was washed with brine (200 mL) then dried (MgSO$_4$), filtered and concentrated in vacuo. Purification of the crude residue by flash column chromatography on silica gel (30% EtOAc/hexane) afforded 2.42 g (97%) of aldehyde 4.

Step 4. Wittig Reaction of 4 to Give 5

Potassium tert-butoxide (2.54 g, 22.6 mmol) was added to a solution of methoxymethyltriphenylphosphonium chloride (3.72 g, 10.8 mmol) in THF (60 mL) at 0° C. After 30 minutes at 0° C., a solution of aldehyde 4 (2.5 g, 9.03 mmol) in THF (30 mL) was added. The reaction mixture was allowed to warm to room temperature and stirred overnight. The reaction was quenched at 0° C. by the slow addition of H$_2$O then was partitioned between 10% aqueous HCl (95 mL) and EtOAc (100 mL). The phases were separated and the aqueous phase was extracted with EtOAc (2×50 mL). The combined organic phase was washed with brine (20 mL) then dried (MgSO$_4$), filtered and concentrated in vacuo. Purification of the crude residue by flash column chromatography on silica gel (40% EtOAc/hexane) afforded 2.70 g (98%) of enol ether 5.

Step 5. Hydrolysis of 5 to Give 6

M aqueous HCl (2.84 mL, 0.28 mmol) was added to a solution of enol ether 5 (2.70 g, 8.86 mmol) in dioxane (90 mL). After 1 hour at room temperature, the mixture was heated at 60° C. for 2.5 hours then cooled to room temperature. The reaction mixture was partitioned between saturated aqueous NaHCO$_3$ (300 mL) and CH$_2$Cl$_2$ (300 mL). The phases were separated and the aqueous phase was extracted with CH$_2$Cl$_2$ (2×300 mL). The combined organic phase was washed with H$_2$O and brine then dried (MgSO$_4$), filtered and concentrated in vacuo. Purification of the crude residue by flash column chromatography on silica gel (30% EtOAc/hexane) afforded 812 mg (32%) of aldehyde 6.

Step 6. Reduction of 6 to Give 7

Sodium borohydride (159 mg, 4.20 mmol) was added to a solution of aldehyde 6 (812 mg, 2.79 mmol) in MeOH (34 mL) at 0° C. The mixture was allowed to warm to room temperature. After 20 minutes at room temperature, the reaction was cooled to 0° C. and quenched by the slow addition of water. The mixture was then diluted with water (200 mL) and extracted with EtOAc (2×300 mL). The combined organic phase was washed with brine, dried (MgSO$_4$), filtered and concentrated in vacuo. Purification of the crude residue by flash column chromatography on silica gel (50% EtOAc/hexane) afforded 816 mg (99%) of alcohol 7.

Step 7. Protection of 7 to Give 8

Pyridine (247 µL, 3.05 mmol) and acetyl chloride (216 µL, 3.04 mmol) were added sequentially to a solution of alcohol 7 (816 mg, 2.79 mmol) in CH$_2$Cl$_2$ (15 mL). After 5 min, the reaction mixture was partitioned between saturated aqueous NaHCO$_3$ (150 mL) and CH$_2$Cl$_2$ (150 mL). The phases were separated and the aqueous phase was extracted with CH$_2$Cl$_2$ (2×150 mL). The combined organic phases were washed with brine (150 mL), dried (MgSO$_4$), filtered and concentrated in vacuo. Purification of the crude residue by flash column chromatography on silica gel (10% EtOAc/hexane) afforded 850 mg (91%) of acetate 8.

Step 8. Deprotection of 8 to Give 9

2,3-Dichloro-5,6-dicyano-1,4-benzoquinone (DDQ, 814 mg, 3.59 mmol) was added to a mixture of ether 8 (400 mg, 1.19 mmol) in CH$_2$Cl$_2$ (9 mL) and H$_2$O (0.45 mL) at 0° C. After 1 hour at 0° C. the reaction was allowed to warm to room temperature. After 4 hours at room temperature, the reaction was quenched with saturated aqueous NaHCO$_3$ (100 mL). The mixture was extracted with CH$_2$Cl$_2$ (3×100 mL). The combined extracts were washed with water and brine then dried (MgSO$_4$), filtered and concentrated in vacuo. Purification of the residue by flash column chromatography on silica gel (30% EtOAc/hexane) afforded 80 mg (31%) of the title compound (9).

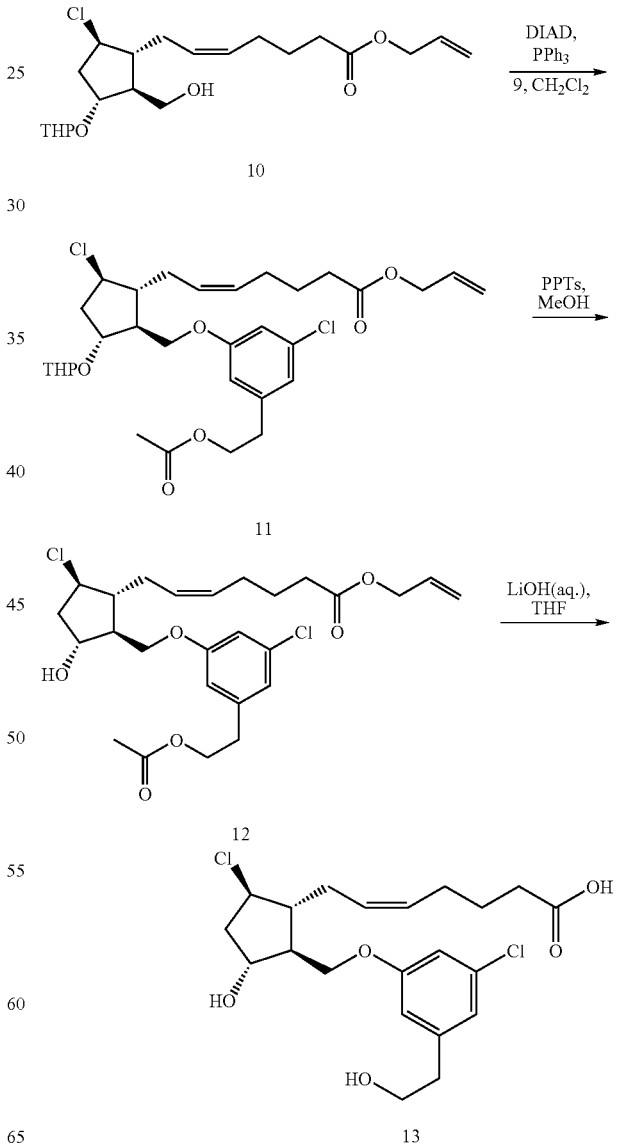

Scheme 2

EXAMPLE 1

(Z)-7-{(1R,2S,3R,5R)-5-Chloro-2-[3-chloro-5-(2-hydroxyethyl)-phenoxymethyl]-3-hydroxy-cyclopentyl}-hept-5-enoic acid (13, Scheme 2)

Step 1. Mitsunobu Reaction of 9 and 10 to Give 11

Triphenylphosphine (98 mg, 0.37 mmol) and diisopropyl azodicarboxylate (DIAD, 58 µL, 0.30 mmol) were added sequentially to a solution of alcohol 10 (see U.S. Provisional Patent Application No. 60/757,696, filed Jan. 10, 2006; 100 mg, 0.25 mmol) and phenol 9 (preparation 1, 80 mg, 0.37 mmol) in CH$_2$Cl$_2$ (1.0 mL). After stirring 18 hours at room temperature, the reaction mixture was partitioned between saturated aqueous NaHCO$_3$ (20 mL) and CH$_2$Cl$_2$ (15 mL). The phases were separated and the aqueous phase was extracted with CH$_2$Cl$_2$ (2×20 mL). The combined organic phase was washed with brine (15 mL), dried (MgSO$_4$), filtered and concentrated in vacuo. Purification of the residue by flash column chromatography on silica gel (20% EtOAc/hexane) afforded 108 mg (72%) of aryl ether 11.

Step 2. Deprotection of 11 to Give 12.

Pyridinium p toluenesulfonate (PPTs, 4.7 mg, 0.019 mmol) was added to a solution of 11 (108 mg, 0.18 mmol) in methanol (2.0 mL) at room temperature under nitrogen. The solution was heated at 40° C. for 5 h, then cooled and concentrated in vacuo. Purification of the crude residue by flash column chromatography on silica gel (50% EtOAc/hexane) afforded 53 mg (57%) of alcohol 12.

Step 3: Hydrolysis of 12 to Give 13

Lithium hydroxide (0.15 mL of a 1.0 M aqueous solution, 0.15 mmol) was added to a solution of ester 12 (13 mg, 0.025 mmol) in THF (0.13 mL). After 2 hours room temperature, the reaction was partitioned between 10% aqueous HCl (3 mL) and EtOAc (7 mL). The phases were separated and the aqueous phase was extracted with EtOAc (2×7 mL). The combined organic phase was washed with brine, dried (MgSO$_4$), filtered and concentrated in vacuo to afford 11 mg (quant.) of the title compound (13).

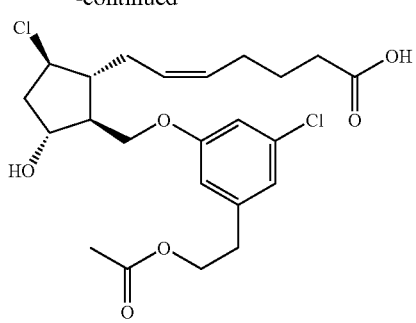

14

EXAMPLE 2

(Z)-7-{(1R,2S,3R,5R)-2-[3-(2-Acetoxy-ethyl)-5-chloro-phenoxymethyl]-5-chloro-3-hydroxy-cyclopentyl}-hept-5-enoic acid (14, Scheme 3)

Tetrakis(triphenylphosphine)palladium(0) (20 mg, 0.017 mmol) and pyrrolidine (14 µL, 0.17 mmol) were added sequentially to a solution of allyl ester 12 (30 mg, 0.058 mmol) in CH$_2$Cl$_2$ (1.0 mL). After 5 min the reaction mixture was partitioned between 1.0 M aqueous HCl (5 mL) and CH$_2$Cl$_2$ (15 mL). The phases were separated and the aqueous phase was extracted with CH$_2$Cl$_2$ (2×10 mL). The combined extracts were washed with brine (10 mL), dried (MgSO$_4$), filtered and concentrated in vacuo. Purification of the crude residue by flash column chromatography on silica gel (60% EtOAc/hexane) afforded 9 mg (33%) of the title compound (14).

Scheme 4

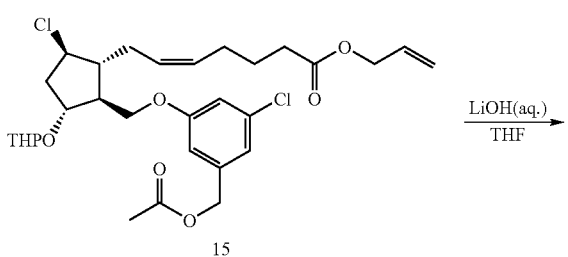

Scheme 3

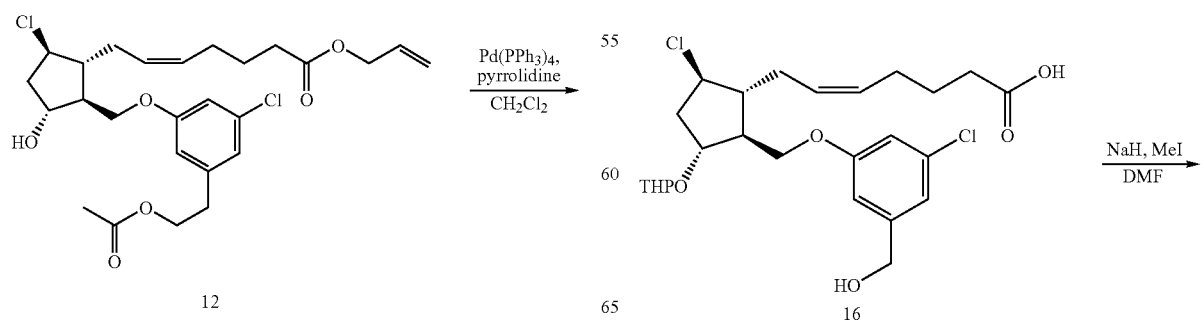

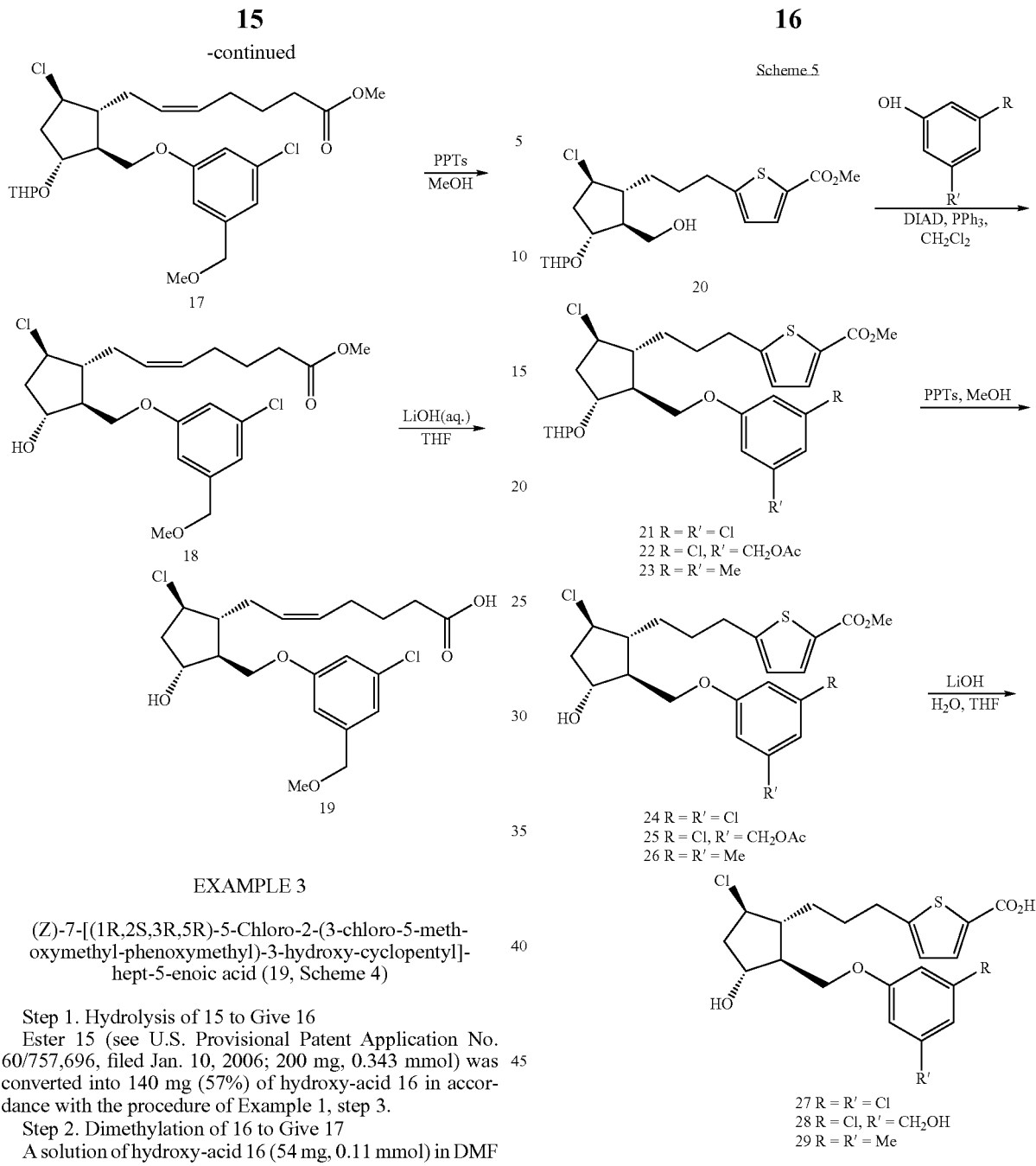

EXAMPLE 3

(Z)-7-[(1R,2S,3R,5R)-5-Chloro-2-(3-chloro-5-methoxymethyl-phenoxymethyl)-3-hydroxy-cyclopentyl]-hept-5-enoic acid (19, Scheme 4)

Step 1. Hydrolysis of 15 to Give 16

Ester 15 (see U.S. Provisional Patent Application No. 60/757,696, filed Jan. 10, 2006; 200 mg, 0.343 mmol) was converted into 140 mg (57%) of hydroxy-acid 16 in accordance with the procedure of Example 1, step 3.

Step 2. Dimethylation of 16 to Give 17

A solution of hydroxy-acid 16 (54 mg, 0.11 mmol) in DMF (0.5 mL) was added to a suspension of sodium hydride (11 mg of a 60 wt. % suspension, 0.28 mmol) in DMF (0.5 mL). Iodomethane (67 L, 1.08 mmol) was then added. The reaction mixture was partitioned between water (5 mL) and EtOAc (10 mL). The phases were separated and the aqueous phase was extracted with EtOAc (2×10 mL). The combined extracts were washed with brine (10 mL), dried ($MgSO_4$), filtered and concentrated in vacuo. Purification of the crude residue by flash column chromatography on silica gel (hexanes→EtOAc, gradient) afforded 50 mg (88%) of 17.

Step 3. Deprotection of 17 to Give 18

Acetal 17 (50 mg, 0.094 mmol) was converted into 23 mg (55%) of alcohol 18 in accordance with the procedure of Example 1, step 2.

Step 4. Hydrolysis of 18 to Give 19

Ester 18 (23 mg, 0.052 mmol) was converted into 13 mg (58%) of the title compound (19) in accordance with the procedure of Example 1, step 3.

EXAMPLE 4

5-{3-[(1R,2S,3R,5R)-5-Chloro-2-(3,5-dichloro-phenoxymethyl)-3-hydroxy-cyclopentyl]-propyl}-thiophene-2-carboxylic acid (27, Scheme 5)

Step 1. Mitsunobu Reaction of 20 to Give 21

Triphenylphosphine (38 mg, 0.14 mmol) and DIAD (23 μL, 0.12 mmol) were added to a solution of alcohol 20 (see U.S. Provisional Patent Application No. 60/805,285, filed Jun. 20, 2006, incorporated by reference herein; 40 mg, 0.096 mmol) and 3,5-dichlorophenol (23 mg, 0.14 mmol) in $CH_2Cl_2$ (1.0 mL). After stirring 18 hours at room temperature, the mixture was partitioned between $CH_2Cl_2$ (10 mL) and saturated aqueous $NaHCO_3$ (10 mL). The phases were separated and the aqueous phase was extracted with $CH_2Cl_2$ (2×10 mL). The combined organic phase was washed with brine (10 mL), dried (MgSO$_4$), filtered and concentrated in vacuo. Purification of the residue by flash column chromatography on silica gel (hexane→EtOAc, gradient) afforded 20 mg (37%) of 21.

Step 2. Deprotection of 21 to Give 24

Pyridinium p-toluenesulfonate (PPTs, 1 mg, 0.004 mmol) was added to a solution of 21 (20 mg, 0.036 mmol) in methanol (0.35 mL) at room temperature. The solution was heated at 40° C. overnight, then cooled and concentrated in vacuo. Purification of the crude residue by flash column chromatography on silica gel (hexane→EtOAc, gradient) afforded 10 mg (59%) of 24.

Step 3. Hydrolysis of 24 to Give 27

Ester 24 (10 mg, 0.021 mmol) was converted into 3 mg (31%) of the title compound (27) in accordance with the procedure of Example 1, step 3 with the following modifications: the reaction was stirred for 18 hours at room temperature, and the crude product was purified by flash column chromatography on silica gel (10% MeOH/CH$_2$Cl$_2$).

EXAMPLE 5

5-{3-[(1R,2S,3R,5R)-5-Chloro-2-(3-chloro-5-hydroxymethyl-phenoxymethyl)-3-hydroxy-cyclopentyl]-propyl}-thiophene-2-carboxylic acid (28, Scheme 5)

Ester 25 (see U.S. Provisional Patent Application No. 60/805,285, filed Jun. 20, 2006; 30 mg, 0.058 mmol) was converted into 13 mg (49%) of the title compound (28) in accordance with the procedure of Example 4, step 3.

EXAMPLE 6

5-{3-[(1R,2S,3R,5R)-5-Chloro-2-(3,5-dimethyl-phenoxymethyl)-3-hydroxy-cyclopentyl]-propyl}-thiophene-2-carboxylic acid (29, Scheme 5)

Step 1. Mitsunobu Reaction of 20 to Give 23

Triphenylphosphine (47 mg, 0.18 mmol) and DIAD (27 µL, 0.14 mmol) were added to a solution of alcohol 20 (see U.S. Provisional Patent Application No. 60/805,285, filed Jun. 20, 2006; 50 mg, 0.12 mmol) and 3,5-dimethylphenol (17 mg, 0.14 mmol) in CH$_2$Cl$_2$ (0.6 mL). After stirring 18 hours at room temperature, the mixture was partitioned between CH$_2$Cl$_2$ (10 mL) and saturated aqueous NaHCO$_3$ (10 mL). The phases were separated and the aqueous phase was extracted with CH$_2$Cl$_2$ (2×10 mL). The combined organic phase was washed with brine (10 mL), dried (MgSO$_4$), filtered and concentrated in vacuo. Purification of the residue by flash column chromatography on silica gel (hexane→EtOAc, gradient) afforded 53 mg (85%) of 23.

Step 2. Deprotection of 23 to Give 26

Acetal 23 (53 mg, 0.10 mmol) was converted into 37 mg (83%) of alcohol 26 in accordance with the procedure of Example 4, step 2

Step 3. Hydrolysis of 26 to Give 29

Ester 26 (37 mg, 0.085 mmol) was converted into 15 mg (42%) of the title compound (29) in accordance with the procedure of Example 1, step 3 with the following modifications: the reaction was stirred for 18 hours at 40° C., and the crude product was purified by flash column chromatography on silica gel (10% MeOH/CH$_2$Cl$_2$).

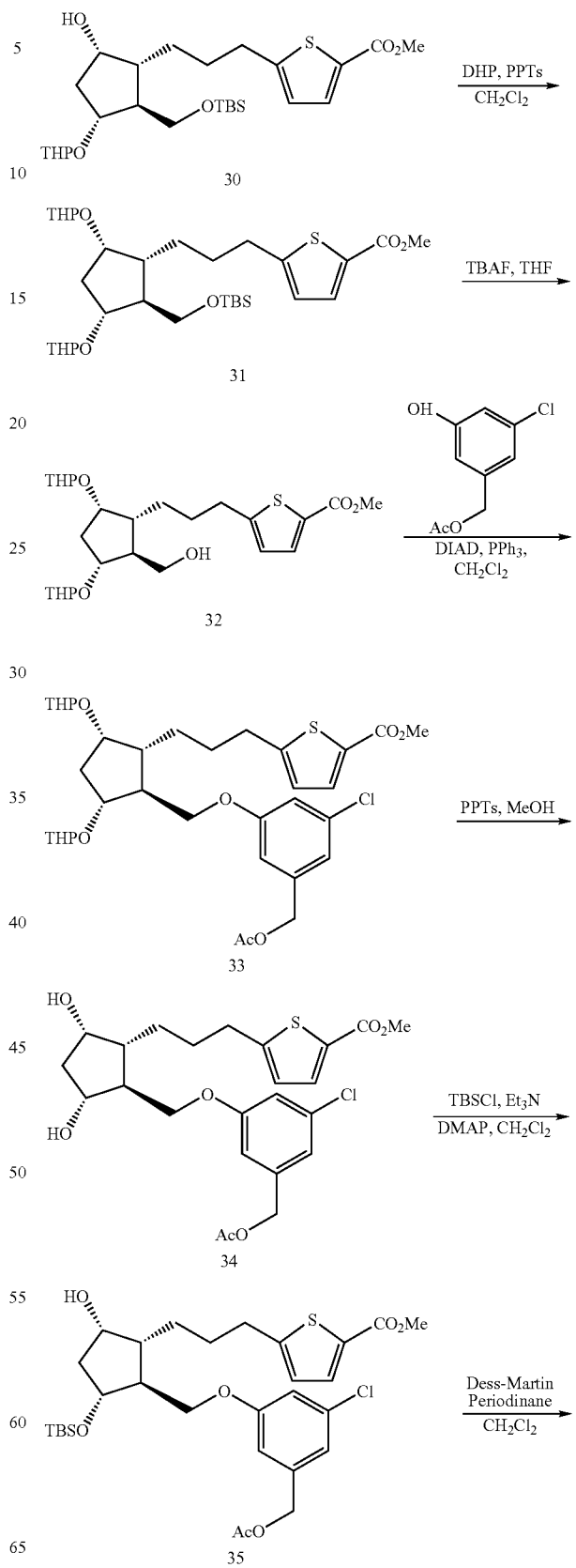

Scheme 6

-continued

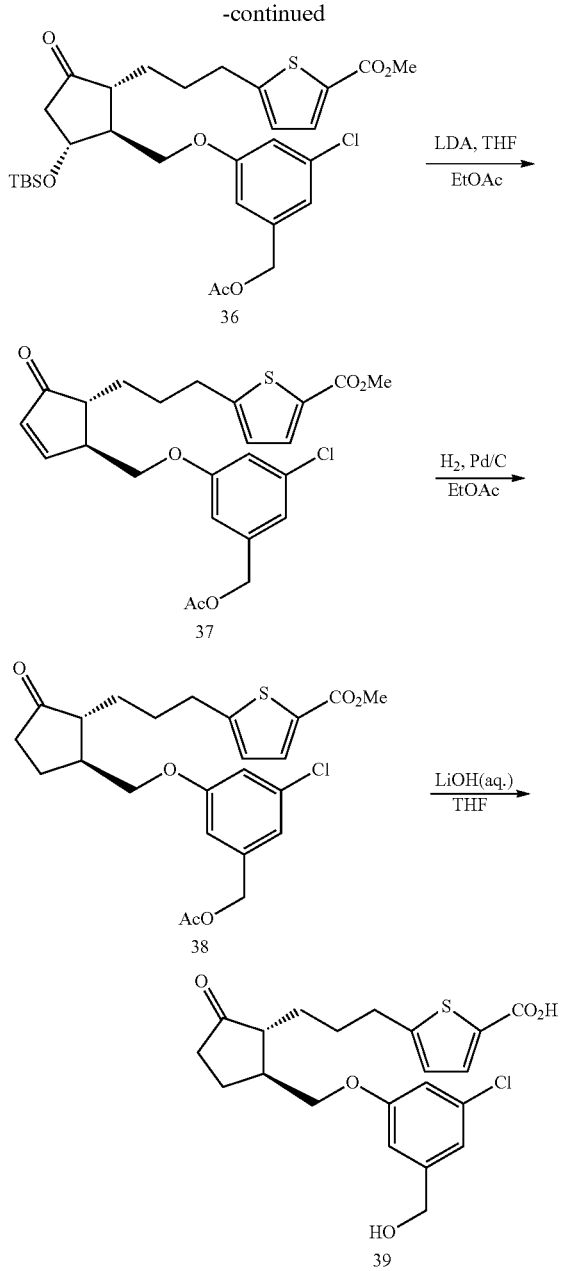

EXAMPLE 7

5-{3-[(1R,2S)-2-(3-Chloro-5-hydroxymethyl-phenoxymethyl)-5-oxo-cyclopentyl]-propyl}-thiophene-2-carboxylic acid (39, Scheme 6)

Step 1. Protection of 30 to Give 31

Dihydropyran (391 μL, 4.29 mmol) and PPTs (50 mg, 0.20 mmol) were added to a solution of alcohol 30 (see U.S. Provisional Patent Application No. 60/805,285, filed Jun. 20, 2006; 550 mg, 1.07 mmol) in $CH_2Cl_2$ (3.0 mL). The reaction mixture was heated at 40° C. overnight, then cooled and concentrated in vacuo. Purification of the crude residue by flash column chromatography on silica gel (hexane→EtOAc, gradient) afforded 550 mg (86%) of 31.

Step 2. Desilylation of 31 to Give 32

Tetrabutylammonium fluoride (2.51 mL of a 1.0 M THF solution, 2.51 mmol) was added to a solution of 31 (500 mg, 0.84 mmol) in THF (7.6 mL). After 18 hours at room temperature, the reaction mixture was partitioned between water (10 mL) and EtOAc (20 mL). The phases were separated and the aqueous phase was extracted with EtOAc (2×10 mL). The combined extracts were washed with brine then dried ($MgSO_4$), filtered and concentrated in vacuo. Purification of the crude residue by flash column chromatography on silica gel (hexane→EtOAc, gradient) afforded 393 mg (97%) of 32.

Step 3. Mitsunobu of 32 to Give 33

Alcohol 32 (437 mg, 0.91 mmol) and 3-chloro-5-hydroxybenzyl acetate (see U.S. Provisional Patent Application No. 60/757,696, filed Jan. 10, 2006; 218 mg, 1.09 mmol) were converted into 350 mg (58%) of aryl ether 33 in accordance with the procedure of Example 6, step 1.

Step 4. Deprotection of 33 to Give 34

Bis-acetal 33 (350 mg, 0.53 mmol) was converted into 150 mg (57%) of diol 34 in accordance with the procedure of Example 4, step 2.

Step 5. Monosilylation of 34 to Give 35

Triethylamine (63 CL, 0.45 mmol), dimethylaminopyridine (7 mg, 0.057 mmol), and tert-butyldimethylsilyl chloride (50 mg, 0.33 mmol) were sequentially added to a solution of 34 (150 mg, 0.30 mmol) in $CH_2Cl_2$ (1.5 mL). After stirring 18 hours at room temperature, the mixture was partitioned between $CH_2Cl_2$ (10 mL) and saturated aqueous $NaHCO_3$ (5 mL). The phases were separated and the aqueous phase was extracted with $CH_2Cl_2$ (2×10 mL). The combined organic phase was washed with brine (10 mL), dried ($MgSO_4$), filtered and concentrated in vacuo. Purification of the residue by flash column chromatography on silica gel (hexane→EtOAc, gradient) afforded 90 mg (49%) of 35.

Step 6. Oxidation of 35 to Give 36

Dess-Martin periodinane (75 mg, 0.18 mmol) was added to a solution of 35 (90 mg, 0.15 mmol) in $CH_2Cl_2$ (7.35 mL) at 0° C. and the mixture was allowed to warm to room temperature. After 2 hours at room temperature, the mixture was partitioned between $CH_2Cl_2$ (10 mL) and water (10 mL). The phases were separated and the aqueous phase was extracted with $CH_2Cl_2$ (2×10 mL). The combined organic phase was washed with brine (5 mL), dried ($MgSO_4$), filtered and concentrated in vacuo. Purification of the residue by flash column chromatography on silica gel (hexane→EtOAc, gradient) afforded 80 mg (89%) of ketone 36.

Step 7. Elimination of 36 to Give 37

A solution of lithium diisopropylamide (0.41 mL of a 2.0 M solution in heptane-THF-ethylbenzene, 0.82 mmol) was added to a solution of 36 (80 mg, 0.13 mmol) in THF (2.3 mL) at −78° C. After 90 minutes at −78° C., the mixture was allowed to warm to room temperature. After 15 minutes at room temperature, the reaction was quenched by the addition of 0.1 N aqueous HCl (15 mL), and extracted with EtOAc (3×20 mL). The combined extracts were washed with brine, dried ($MgSO_4$), filtered and concentrated in vacuo. Purification of the residue by flash column chromatography on silica get (hexane→EtOAc, gradient) afforded 40 mg (64%) of enone 37.

Step 8. Hydrogenation of 37 to Give 38

Palladium on carbon (10 wt. %, 8 mg) was added to a solution of enone 37 (40 mg, 0.084 mmol) in EtOAc (1.6 mL). A hydrogen atmosphere was established by evacuating and refilling with hydrogen (5×) and the reaction mixture was stirred under a balloon of hydrogen for 18 hours. The reaction mixture was filtered through celite, washing with EtOAc, and the filtrate was concentrated in vacuo to afford 31 mg (77%) of saturated ketone 38.

Step 9. Hydrolysis of 38 to Give 39

Ester 38 (5 mg, 0.010 mmol) was converted into 3.5 mg (79%) of the title compound (39) in accordance with the procedure of Example 4, step 3.

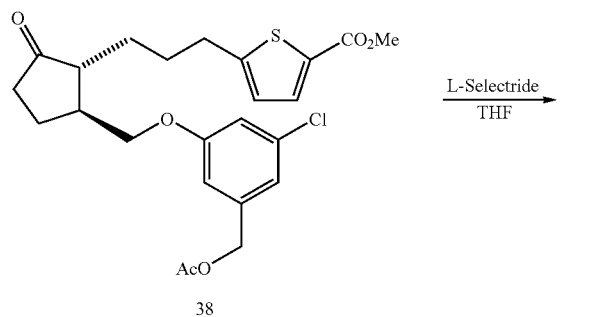

Scheme 7

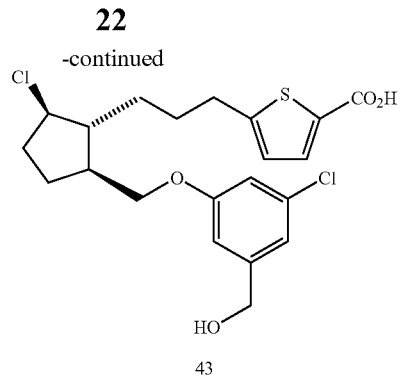

43

EXAMPLE 8

5-{3-[(1R,2R,5S)-2-Chloro-5-(3-chloro-5-hydroxymethyl-phenoxymethyl)-cyclopentyl]-propyl}-thiophene-2-carboxylic acid (43, Scheme 7)

Step 1. Reduction of 38 to Give 40

A solution of L-selectride (74 µL of a 1.0 M solution in THF, 0.074 mmol) was added to a solution of 38 (26 mg, 0.054 mmol) in THF (1.8 mL) at −78° C. After 1 hour at −78° C., additional L-selectride (108 µL, 0.108 mmol) was added. After 5 hours at −78° C., the reaction was quenched by the addition of 3% aqueous $H_2O_2$ (1.5 mL) and the mixture was allowed to warm to room temperature. Water (5 mL) was added and the mixture was extracted with EtOAc (2×10 mL). The combined extracts were dried ($MgSO_4$), filtered and concentrated in vacuo. Purification of the residue by flash column chromatography on silica gel (hexane→EtOAc, gradient) afforded 13 mg (50%) of alcohol 40.

Step 2. Mesylation of 40 to Give 41

Triethylamine (5.6 µL, 0.040 mmol) and methanesulfonyl chloride (2.6 µL, 0.033 mmol) were added sequentially to a solution of 40 (13 mg, 0.027 mmol) in $CH_2Cl_2$ (0.2 mL) at 0° C., and reaction was allowed to warm to room temperature. After 18 hours at room temperature, saturated aqueous $NaHCO_3$ (5 mL) was added and the mixture was extracted with $CH_2Cl_2$ (3×5 mL). The combined extracts were washed with brine (2 mL), dried ($MgSO_4$), filtered and concentrated in vacuo to afford 15 mg (99%) of mesylate 41.

Step 3. Conversion of 41 to Chloride 42

Tetrabutylammonium chloride (38 mg, 0.14 mmol) was added to a solution of 41 (15 mg, 0.027 mmol) in toluene (0.27 mL). The reaction mixture was heated at 50° C. for 18 hours. The cooled mixture was diluted with brine (10 mL) and extracted with EtOAc (3×25 mL). The combined organic extracts were dried ($MgSO_4$), filtered and concentrated in vacuo. Purification of the crude residue by gash column chromatography on silica gel (hexane→EtOAc, gradient) afforded 5 mg (37%) of chloride 42.

Step 4. Hydrolysis of 42 to Give 43

Ester 42 (5 mg, 0.010 mmol) was converted into 1 mg (23%) of the title compound (43) in accordance with the procedure of Example 4, step 3.

Scheme 8

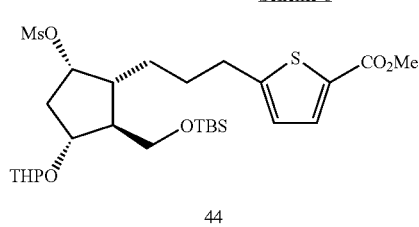

44

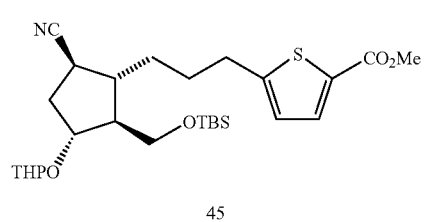

45

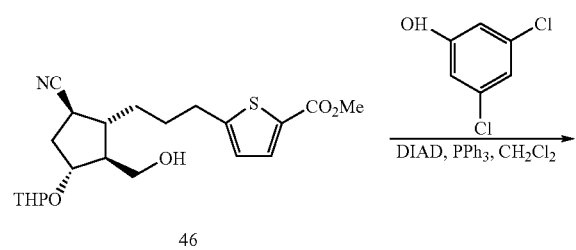

46

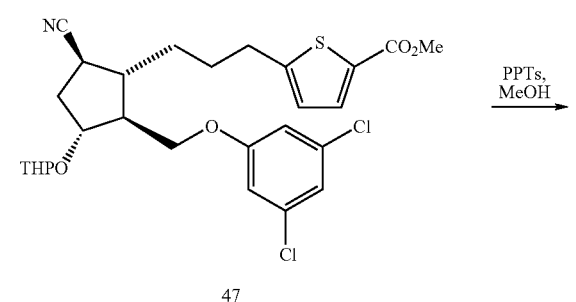

47

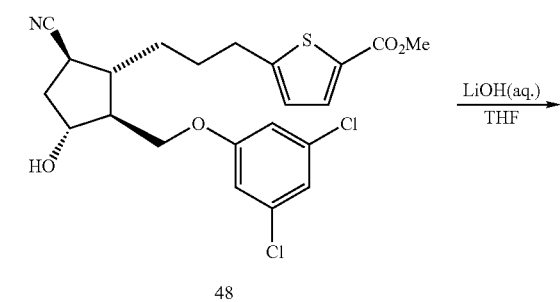

48

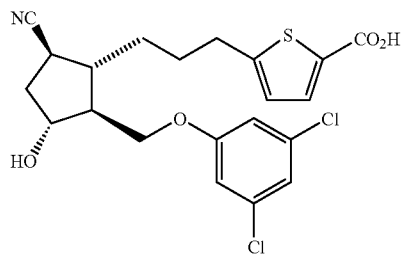

49

EXAMPLE 9

5-{3-[(1S,2S,3R,5R)-5-Cyano-2-(3,5-dichloro-phenoxymethyl)-3-hydroxy-cyclopentyl]-propyl}-thiophene-2-carboxylic acid (49, Scheme 8)

Step 1. Conversion of 44 to Give Nitrile 45

Potassium cyanide (569 mg, 8.74 mmol) was added to a solution of mesylate 44 (see U.S. Provisional Patent Application No. 60/805,285, filed Jun. 20, 2006; 2.10 g, 3.55 mmol) in DMSO (97 mL). The mixture was heated at 65° C. for 18 hours then cooled to room temperature. The mixture was diluted with water (100 mL) and brine (100 mL) and extracted with $CH_2Cl_2$ (3×200 mL). The combined organic phase was dried ($MgSO_4$) filtered and concentrated in vacuo. Purification of the residue by flash column chromatography on silica gel (hexane→EtOAc, gradient) afforded 270 mg (15%) of nitrite 45.

Step 2. Desilylation of 45 to Give 46

Silyl ether 45 (270 mg, 0.52 mmol) was converted into 150 mg (71%) of alcohol 46 in accordance with the procedure of Example 7, step 2.

Step 3. Mitsunobu of 46 to Give 47

Alcohol 46 (50 mg, 0.12 mmol) and 3,5-dichlorophenol (24 mg, 0.15 mmol) were converted into 50 mg (74%) of aryl ether 47 in accordance with the procedure of Example 6, step 1.

Step 4. Deprotection of 47 to Give 48

Acetal 47 (50 mg, 0.090 mmol) was converted into 20 mg (47%) of alcohol 48 in accordance with the procedure of Example 4, step 2.

Step 5. Hydrolysis of 48 to Give 49

Ester 48 (15 mg, 0.032 mmol) was converted into 8 mg (55%) of the title compound (49) in accordance with the procedure of Example 1, step 3 with the following modifications: the concentration was 0.4 M in THF, the reaction was stirred for 18 hours at 40° C., and the crude product was purified by flash column chromatography on silica gel (10% MeOH/$CH_2Cl_2$).

Scheme 9
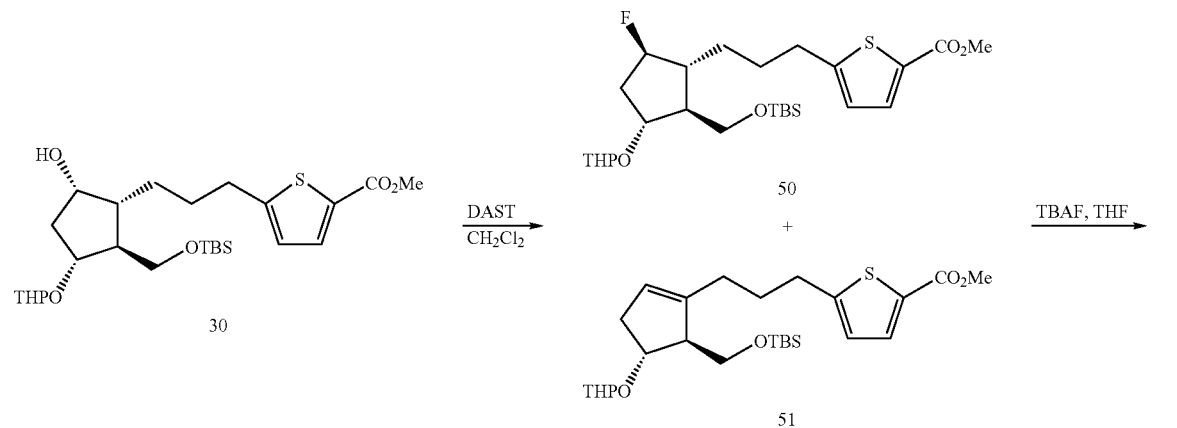
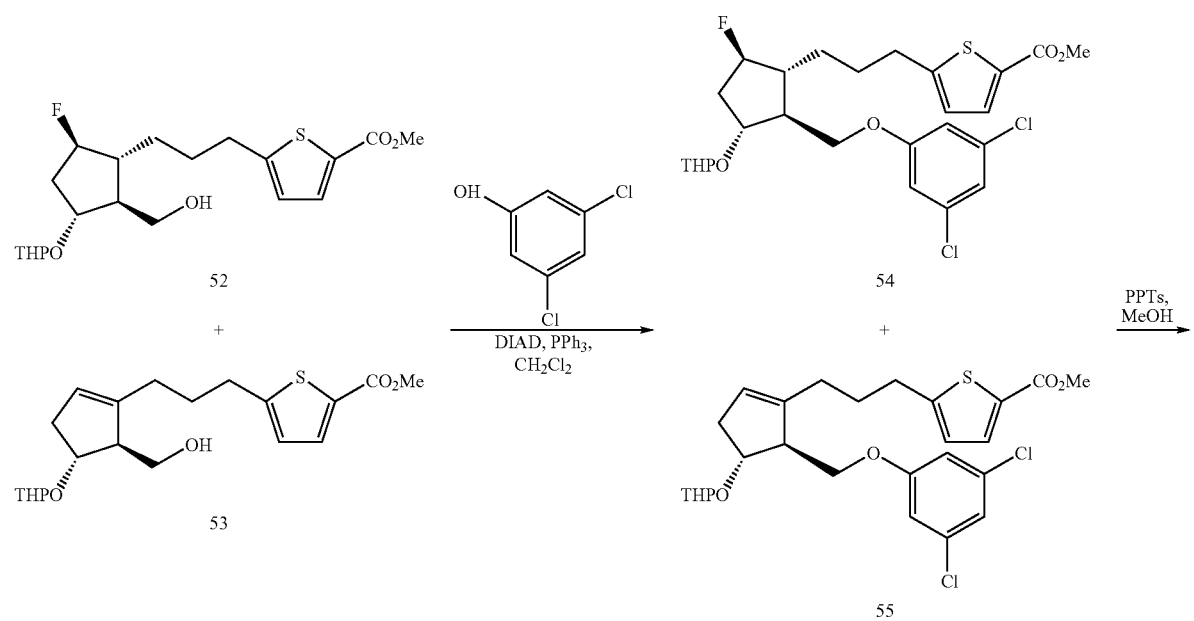

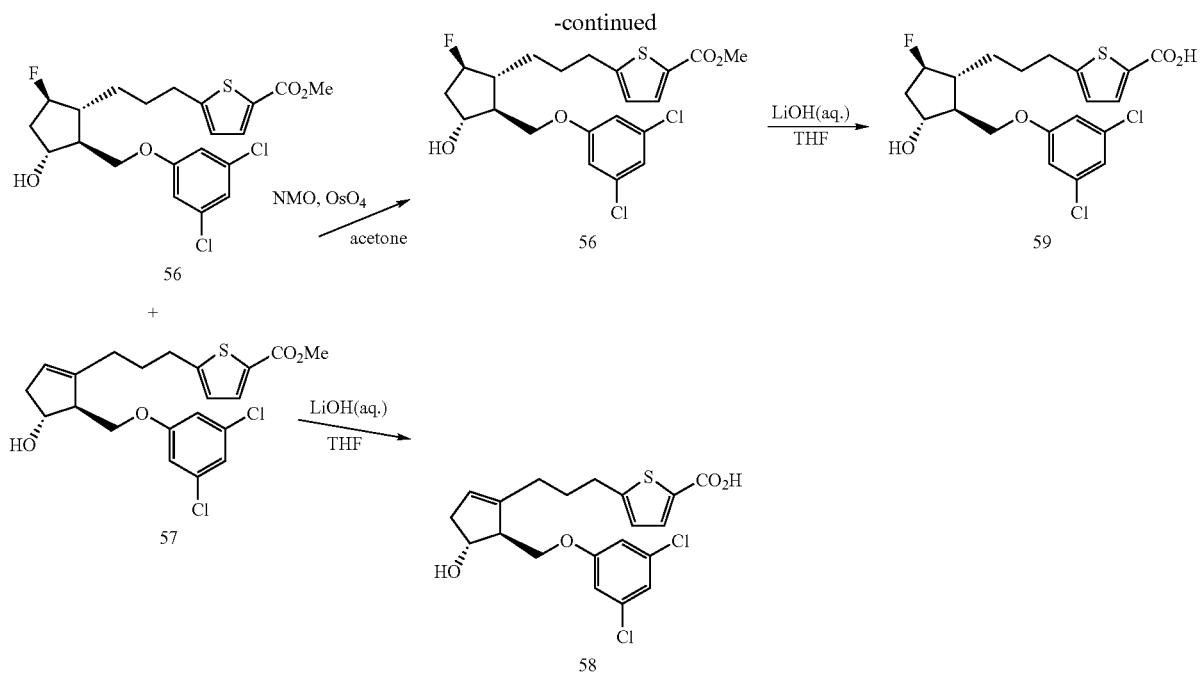

EXAMPLE 10

5-{3-[(4R,5S)-5-(3,5-Dichloro-phenoxymethyl)-4-hydroxy-cyclopent-1-enyl]-propyl}-thiophene-2-carboxylic acid (58, Scheme 9)

Step 1. Conversion of 30 to Fluoride 50 and Alkene 51

(Diethylamino)sulfur trifluoride (DAST, 104 µL, 0.79 mmol) was added to a solution of alcohol 30 (see U.S. Provisional Patent Application No. 60/805,285, filed Jun. 20, 2006; 200 mg, 0.39 mmol) in $CH_2Cl_2$ (92 mL) at −78° C. After 30 minutes at room temperature, the reaction was quenched with saturated aqueous $NaHCO_3$ (25 mL). The mixture was diluted with water (25 mL) and extracted with $CH_2Cl_2$ (2×25 mL). The combined organic phase was dried ($MgSO_4$), filtered and concentrated in vacuo. Purification of the residue by flash column chromatography on silica gel (hexane→EtOAc, gradient) afforded 42 mg (~20%) of an inseparable mixture of 50 and 51.

Step 2. Disilylation of 50/51 to 52/53

Silyl ethers 50/51 (42 mg, ~0.08 mmol) were converted into 25 mg (~77%) of inseparable alcohols 52/53 in accordance with the procedure of Example 7, step 2.

Step 3. Mitsunobu of 52/53 to 54/55

Alcohols 52153 (25 mg, ~0.06 mmol) and 3,5-dichlorophenol (9 mg, 0.055 mmol) were converted into 24 mg (~70%) of inseparable aryl ethers 54/55 in accordance with the procedure of Example 6, step 1.

Step 4. Deprotection of 54/55 to 56 and 57

Acetals 54/55 (24 mg, ~0.45 mmol) were converted into 1 mg (~5%) of hydroxyl alkene 57 and 20 mg (~83%) of a mixture of 56 and 57 in accordance with the procedure of Example 4, step 2.

Step 5. Hydrolysis of 57 to 58

Ester 57 (1 mg, 0.022 mmol) was converted into 1 mg (quant.) of the title compound (58) in accordance with the procedure of Example 6, step 3.

EXAMPLE 11

5-{3-[(1R,2S,3R,5R)-2-(3,5-Dichloro-phenoxymethyl)-5-fluoro-3-hydroxy-cyclopentyl]-propyl}-thiophene-2-carboxylic acid (59, Scheme 9)

Step 1. Oxidation of 56/57 to Afford Pure 56

Osmium tetroxide (160 µL of a 4 wt. % solution in water, 0.026 mmol) was added to a solution of 4-methylmorpholine N-oxide (NMO, 11.4 mg, 0.097 mmol) and the mixture of 56 and 57 (Example 10, step 4, 20 mg, ~0.044 mmol) in acetone (1.1 mL) at 0° C. and the reaction was allowed to warm to room temperature. After 1 h, the reaction was quenched with 5% aqueous $NaHCO_3$ (5 mL) and extracted with EtOAc (3×5 mL). The combined extracts were washed with brine (5 mL), dried ($MgSO_4$), filtered and concentrated in vacuo. Purification of the residue by flash column chromatography on silica gel (hexane→EtOAc, gradient) afforded 5 mg (~24%) of fluoride 56.

Step 2. Hydrolysis of 56 to Give 59

Ester 56 (5 mg, 0.011 mmol) was converted into 2 mg (41%) of the title compound (59) in accordance with the procedure of Example 6, step 3.

Scheme 10

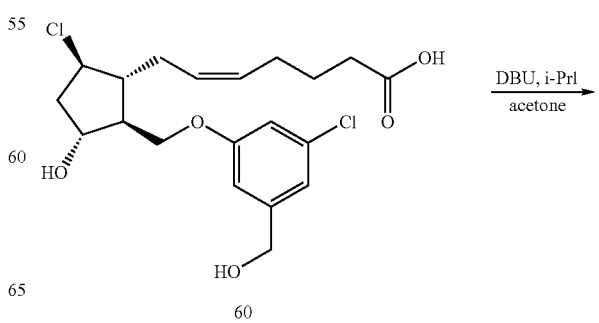

60

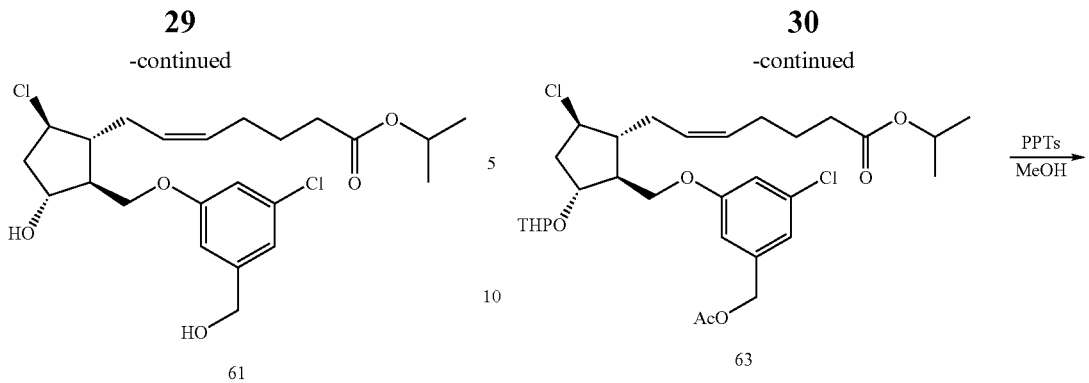

61

EXAMPLE 12

(Z)-Isopropyl 7-((1R,2S,3R,5R)-5-chloro-2-((3-chloro-5-(hydroxymethyl)phenoxy)methyl)-3-hydroxycyclopentyl)hept-5-enoate (61, Scheme 10)

1,8-Diazabicyclo[5.4.0]undec-7-ene (DBU, 19 μL, 0.13 mmol) and 2-iodopropane (167 μL, 1.68 mmol) were added to a solution of acid 60 (U.S. Provisional Patent Application No. 60/757,696, filed Jan. 10, 2006; 35 mg, 0.084 mmol) in acetone (0.8 mL) at room temperature. After 72 hours at room temperature, the reaction diluted with EtOAc (5 mL) and washed with 0.1 N aqueous HCl (2×5 mL) and brine (5 mL), then dried (MgSO$_4$), filtered and concentrated in vacuo. Purification of the residue by Flash column chromatography on silica gel (20% EtOAc/hexane) afforded 6.1 mg (16%) of the title compound (61).

Scheme 11

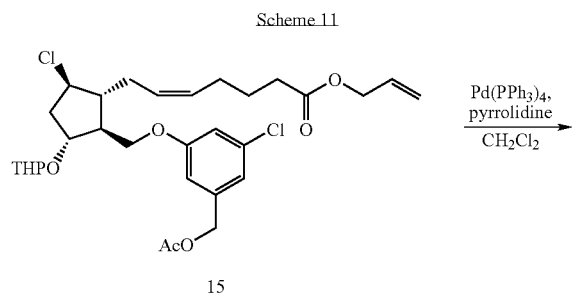

15

EXAMPLE 13

(Z)-Isopropyl 7-((1R,2S,3R,5R)-2-((3-(acetoxymethyl)-5-chlorophenoxy)methyl)-5-chloro-3-hydroxycyclopentyl)hept-5-enoate (64, Scheme 11)

Step 1. Selective Deprotection of 15 to Give 62

Ester 15 (120 mg, 0.21 mmol) was converted into 120 mg (impure with triphenylphosphine) of acid 62 in accordance with the procedure of Example 2, step 1 with the following modifications: the concentration was 0.1 M and 1 equivalent of pyrrolidine was used.

Step 2. Conversion of Acid 62 to Ester 63

Acid 62 (120 mg, 0.21 mmol) was converted into 87 mg (72% for 2 steps) of ester 63 in accordance with the procedure of Example 12.

Step 3. Deprotection of 63 to Give 64

Acetal 63 (87 mg, 0.15 mmol) was converted into 37 mg (50%) of the title compound (64) in accordance with the procedure of Example 4, step 2.

Scheme 12

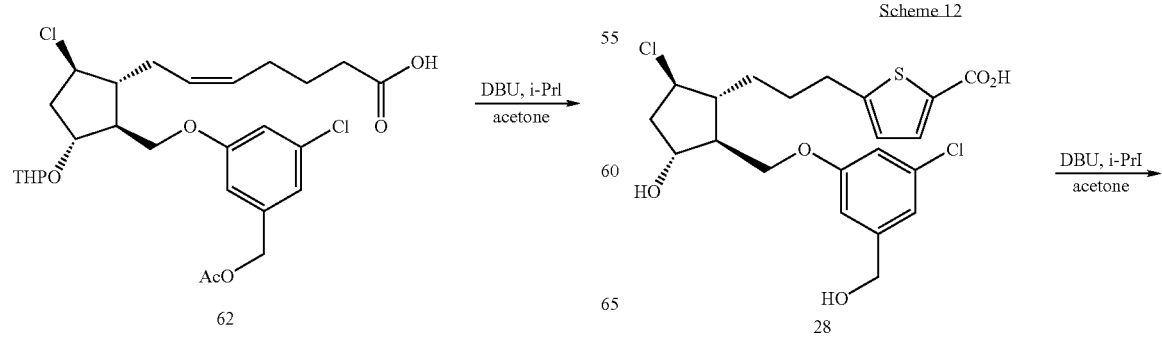

-continued

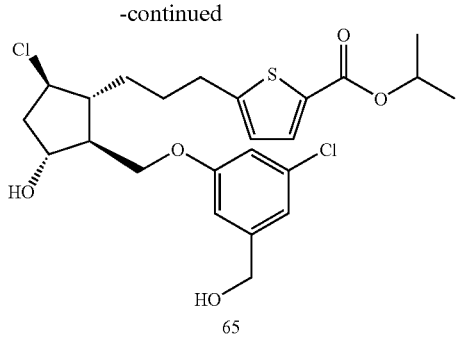
65

EXAMPLE 14

Isopropyl 5-{3-[(1R,2S,3R,5R)-5-Chloro-2-(3-chloro-5-hydroxymethyl-phenoxymethyl)-3-hydroxy-cyclopentyl]-propyl}-thiophene-2-carboxylate (65, Scheme 12)

Acid 28 (8 mg, 0.21 mmol) was converted into 3 mg (34%) of the title compound (65) in accordance with the procedure of Example 12.

In accordance with the procedures of example 4, steps 1-3, alcohol 20 and the appropriate phenol derivative were converted into the title compounds.

5-(3-((1R,2S,3R,5R)-5-chloro-2-((4-chloronaphthalen-1-yloxy)methyl)-3-hydroxycyclopentyl)propyl)thiophene-2-carboxylic acid 5-(3-((1R,2S,3R,5R)-5-chloro-2-((4-chloro-3,5-dimethylphenoxy)methyl)-3-hydroxycyclopentyl)propyl)thiophene-2-carboxylic acid 5-(3-((1R,2S,3R,5R)-5-chloro-2-((3,5-difluorophenoxy)methyl)-3-hydroxycyclopentyl)propyl)thiophene-2-carboxylic acid 5-(3-((1R,2S,3R,5R)-5-chloro-2-((3-fluoro-5-(trifluoromethyl)phenoxy)methyl)-3-hydroxycyclopentyl)propyl)thiophene-2-carboxylic acid 5-(3-((1R,2S,3R,5R)-5-chloro-3-hydroxy-2-(phenoxymethyl)cyclopentyl)propyl)thiophene-2-carboxylic acid 5-(3-((1R,2S,3R,5R)-5-chloro-2-((4-heptylphenoxy)methyl)-3-hydroxycyclopentyl)propyl)thiophene-2-carboxylic acid 5-(3-((1R,2S,3R,5R)-5-chloro-3-hydroxy-2-((naphthalen-1-yloxy)methyl)cyclopentyl)propyl)thiophene-2-carboxylic acid 5-(3-((1R,2S,3R,5R)-5-chloro-3-hydroxy-2-((naphthalen-2-yloxy)methyl)cyclopentyl)propyl)thiophene-2-carboxylic acid 5-(3-((1R,2S,3R,5R)-5-chloro-2-((3-ethylphenoxy)methyl)-3-hydroxycyclopentyl)propyl)thiophene-2-carboxylic acid 5-(3-((1R,2S,3R,5R)-5-chloro-3-hydroxy-2-((3-propylphenoxy)methyl)cyclopentyl)propyl)thiophene-2-carboxylic acid 5-(3-((1R,2S,3R,5R)-5-chloro-3-hydroxy-2-((5,6,7,8-tetrahydronaphthalen-1-yloxy)methyl)cyclopentyl)propyl)thiophene-2-carboxylic acid 5-(3-((1R,2S,3R,5R)-5-chloro-3-hydroxy-2-((5,6,7,8-tetrahydronaphthalen-2-yloxy)methyl)cyclopentyl)propyl)thiophene-2-carboxylic acid 5-(3-((1R,2S,3R,5R)-5-chloro-2-((4-chloro-3-ethylphenoxy)methyl)-3-hydroxycyclopentyl)propyl)thiophene-2-carboxylic acid

In Vitro Testing

U.S. patent application Ser. No. 11/553,143, filed on Oct. 26, 2006, describes the methods used to obtain the in vitro data in the table below.

| | hEP2 | | | hEP4 | | Other Receptors | | | | | |
|---|---|---|---|---|---|---|---|---|---|---|---|
| | flipr | cAMP | | flipr | | | | | | | |
| Structure | EC50 | EC50 | Ki | EC50 | Ki | hFP | hEP1 | hEP3 | hTP | hIP | hDP |
| | 644 | 7 | 107 | NA | NA | | | 8825 | >10000 | NA | >10000 |

-continued

| Structure | hEP2 | | | hEP4 | | Other Receptors | | | | | |
|---|---|---|---|---|---|---|---|---|---|---|---|
| | flipr EC50 | cAMP EC50 | Ki | flipr EC50 | Ki | hFP | hEP1 | hEP3 | hTP | hIP | hDP |
| (structure 1) | 4985 | 18 | 82 | NA | | | | | | | |
| (structure 2) | 3410 | 8 | 39 | 4819 | 1452 | NA | 5184 | 7215 | >10000 | NA | NA |
| (structure 3) | 7006 | 0.12 | 2 | >10000 | 366 | NA | NA | NA | NA | NA | NA |
| (structure 4) | 3278 | 0.26 | 3 | >10000 | | NA | NA | NA | NA | NA | NA |
| (structure 5) | 31 | 0.2 | 2 | 2937 | 158 | NA | NA | NA | NA | NA | NA |

-continued

| Structure | hEP2 flipr EC50 | hEP2 cAMP EC50 | hEP2 Ki | hEP4 flipr EC50 | hEP4 Ki | Other Receptors hFP | hEP1 | hEP3 | hTP | hIP | hDP |
|---|---|---|---|---|---|---|---|---|---|---|---|
| (structure) | 297 | 2 | 39 | >10000 | 179 | NA | NA | NA | NA | NA | NA |
| (structure) | 6753 | 5.2 | 12 | >10000 | 197 | NA | NA | NA | NA | NA | NA |
| (structure) | 15 | 0.2 | 3 | >10000 | 149 | NA | NA | NA | NA | NA | NA |
| (structure) | 424 | 4.8 | 81 | >10000 | 1584 | NA | NA | NA | NA | NA | NA |
| (structure) | 83 | 0.7 | 8 | >10000 | 310 | NA | NA | NA | NA | NA | NA |

-continued

| Structure | hEP2 | | | hEP4 | | Other Receptors | | | | | |
|---|---|---|---|---|---|---|---|---|---|---|---|
| | flipr EC50 | cAMP EC50 | Ki | flipr EC50 | Ki | hFP | hEP1 | hEP3 | hTP | hIP | hDP |
| (Cl-cyclopentane-OH / 3,5-dichlorophenoxymethyl / pentenoic acid) | 0.8 | 0.9 | 12 | 48 | 940 | NA | >10000 | 1263 | >10000 | NA | >10000 |
| (Cl-cyclopentane-OH / 3-chloro-5-hydroxymethylphenoxy / pentenoic acid) | 520 | 2 | 64 | 10632 | 497 | NA | | 3925 | >10000 | NA | >10000 |

| Structure | EP2 data | | | EP4 data | | Other Receptors (ED50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (Cl-cyclopentane / 4-chloronaphthyloxy / thiophene carboxylate) | 3529 | 2.5 | 10 | 15009 | 1929 | NA | NA | NA | NA | NA | 13539 |
| (Cl-cyclopentane / 3-chloro-5-methylphenoxy / thiophene carboxylate) | 1494 | 0.2 | 0.7 | >10000 | 170 | NA | NA | NA | NA | NA | 7194 |

| Structure | EP2 data | | | EP4 data | | Other Receptors (ED50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| (3,5-difluorophenoxy) | 216 | 0.3 | 3 | 5287 | 1285 | NA | NA | 4139 | NA | NA | 12134 |
| (3-fluoro-5-CF3-phenoxy) | 1146 | 0.2 | 2.4 | 12337 | 354 | NA | NA | 6818 | NA | NA | NA |
| (phenoxy) | 235 | 3.4 | 29 | 8423 | 2323 | NA | NA | 9654 | NA | NA | 9086 |
| (4-heptylphenoxy) | 6823 | 46 | 378 | >10000 | 4523 | NA | NA | NA | NA | NA | NA |
| (1-naphthyloxy) | 949 | 0.7 | 5.5 | >10000 | 114 | NA | NA | 4034 | NA | NA | 4148 |
| (2-naphthyloxy) | >10000 | 3 | 3 | >10000 | 227 | NA | NA | NA | NA | NA | NA |

-continued

| Structure | EP2 data | | | EP4 data | | Other Receptors (ED50 in nM) | | | | | |
| --- | --- | --- | --- | --- | --- | --- | --- | --- | --- | --- | --- |
| | flipr EC50 | cAMP EC50 | Ki | flipr EC50 | KI | hFP | hEP1 | hEP3A | hTP | hIP | hDP |
| (structure) | 447 | 0.4 | 4 | 6743 | 214 | NA | 31463 | 3568 | NA | | 4440 |
| (structure) | 33 | 0.4 | 6 | >10000 | 471 | NA | 17915 | 6516 | NA | NA | NA |
| (structure) | 175 | 2.5 | 37 | 9827 | 1461 | NA | NA | 5791 | NA | NA | 8618 |
| (structure) | 2488 | 12 | 38 | >10000 | 800 | NA | NA | NA | NA | NA | NA |
| (structure) | 31387 | 0.4 | 2 | 26520 | 177 | NA | NA | NA | NA | NA | NA |

In Vivo Testing

U.S. Pat. No. 7,091,231 describes the methods used for these in vivo tests. 5-{3-[1R,2S,3R,5R)-5-Chloro-2-(3,5-dichloro-phenoxymethyl)-3-hydroxy-cyclopentyl]-propyl}-thiophene-2-carboxylic acid was tested at multiple concentrations in normotensive dogs, dosing once daily for 5 days. At 0.1%, the maximum intraocular pressure (IOP) decrease from baseline was 7.5 mmHg (48%) at 30 h; the maximum ocular surface hyperemia (OSH) score was 2.75 at 26 h. At 0.01%, the maximum IOP decrease from baseline was 7.5 mmHg (43%) at 76 h; the maximum OSH score was 2.0 at 26 h. At 0.005%, the maximum IOP decrease from baseline was 6.6 mmHg (35%) at 78 h; the maximum OSH score was 1.75 at 74 h. This compound was also tested in laser-induced hypertensive monkeys, using one single day dose. At 0.01%, the maximum IOP decrease from baseline was 20.2 mmHg (53%) at 24 h.

5-{3-[(1R,2S,3R,5R)-5-Chloro-2-(3-chloro-5-hydroxymethyl-phenoxymethyl)-3-hydroxy-cyclopentyl]-propyl}-thiophene-2-carboxylic acid was tested in normotensive dogs, dosing once daily for 5 days. At 0.1%, the maximum IOP decrease from baseline was 5.2 mmHg (34%) at 4 h; the maximum OSH score was 1.9 at 26 h.

5-{3-[(1R,2S,3R,5R)-5-Chloro-2-(3,5-dimethyl-phenoxymethyl)-3-hydroxy-cyclopentyl]-propyl}-thiophene-2- carboxylic acid was tested in normotensive dogs, dosing once daily for 5 days. At 0.01%, the maximum IOP decrease from baseline was 6.4 mmHg (33%) at 78 h; the maximum OSH score was 1.9 at 74 h.

5-{3-[(1S,2S,3R,5R)-5-Cyano-2-(3,5-dichloro-phenoxymethyl)-3-hydroxy-cyclopentyl]-propyl}-thiophene-2-carboxylic acid was tested in normotensive dogs, dosing once daily for 5 days. At 0.01%, the maximum IOP decrease from baseline was 3.1 mmHg (17%) at 30 h; the maximum OSH score was 1.2 at 26 h.

(Z)-Isopropyl 7-((1R,2S,3R,5R)-5-chloro-2-((3-chloro-5-(hydroxymethyl)phenoxy)methyl)-3-hydroxycyclopentyl) hept-5-enoate was tested in normotensive dogs, dosing once daily for 5 days. At 0.1%, the maximum IOP decrease from baseline was 5.9 mmHg (33%) at 100 h; the maximum OSH score was 0.8 at 28 h. This compound was also tested in laser-induced hypertensive monkeys, using one single day dose. At 0.1%, the maximum IOP decrease from baseline was 7.4 mmHg (21%) at 6 h.

(Z)-Isopropyl 7-((1R,2S,3R,5R)-2-((3-(acetoxymethyl)-5-chlorophenoxy)methyl)-5-chloro-3-hydroxycyclopentyl) hept-5- enoate was tested in normotensive dogs, dosing once daily for 5 days. At 0.1%, the maximum IOP decrease from baseline was 3.4 mmHg (20%) at 94 h; the maximum OSH score was 0.7 at 4 h. This compound was also tested in laser-induced hypertensive monkeys, using one single day dose. At 0.1%, the maximum IOP decrease from baseline was 8.2 mmHg (21%) at 6 h.

Isopropyl 5-(3-((1R,2S,3R,5R)-5-chloro-2-((3-chloro-5-hydroxymethylphenoxy)methyl)-3-hydroxycyclopentyl)-propyl)thiophene-2-carboxylate was tested in normotensive dogs, dosing once daily for 5 days. At 0.1%, the maximum IOP decrease from baseline was 6.1 mmHg (36%) at 6 h; the maximum OSH score was 1.9 at 26 h.

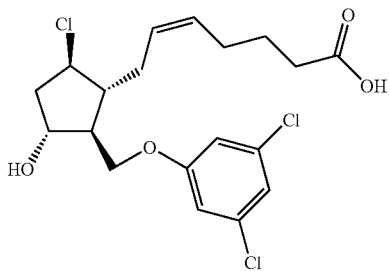

(Z)-7-[(1R,2S,3R,5R)-5-Chloro-2-(3,5-dichloro-phenoxymethyl)-3-hydroxy-cyclopentyl]-hept-5-enoic acid was tested at multiple concentrations in normotensive dogs, dosing once daily for 5 days. At 0.05%, the maximum IOP decrease from baseline was 4.3 mmHg (30%) at 6 h; the maximum OSH score was 0.6 at 6 h. At 0.1%, the maximum IOP decrease from baseline was 4.8 mmHg (34%) at 102 h; the maximum OSH score was 1.3 at 6 h. This compound was also tested in laser-induced hypertensive monkeys, using one single day dose. At 0.1%, the maximum IOP decrease from baseline was 6 mmHg (19%) at 6 h.

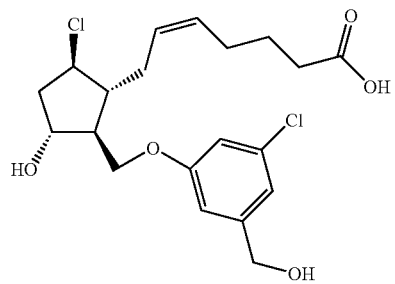

(Z)-7-[(1R,2S,3R,5R)-5-Chloro-2-(3-chloro-5-hydroxymethyl-phenoxymethyl)-3-hydroxy-cyclopentyl]-hept-5-enoic acid was tested in normotensive dogs, dosing once daily for 5 days. At 0.1%, the maximum IOP decrease from baseline was 2.2 mmHg (13.5%) at 26 h; the maximum OSH score was 0.9 at 100 h. This compound was also tested in laser-induced hypertensive monkeys, using one single day dose. At 0.1%, the maximum IOP decrease from baseline was 8 mmHg (21%) at 6 h.

What is claimed is:
1. A compound of the formula

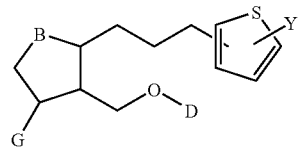

or a pharmaceutically acceptable salt thereof;
wherein Y is an organic acid functional group, or an amide or ester thereof comprising up to 12 carbon atoms; or Y is hydroxymethyl or an ether thereof comprising up to 12 carbon atoms; or Y is a tetrazolyl functional group;
B is C=O, $CH_2$, CHOH, CHCl, CHF, CHBr, or CHCN;
G is OH or H; and
D is substituted phenyl.

2. The compound of claim 1 wherein Y is $CO_2R^2$, CON$(R^2)_2$, CON(OR$^2$)R$^2$, CON(CH$_2$CH$_2$OH)$_2$, CONH(CH$_2$CH$_2$OH), CH$_2$OH, P(O)(OH)$_2$, CONHSO$_2$R$^2$, SO$_2$N$(R^2)_2$, SO$_2$NHR$^2$,

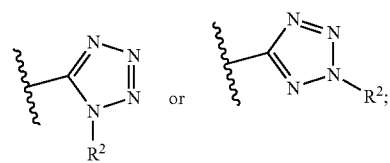

wherein $R^2$ is independently H, $C_1$-$C_6$ alkyl, unsubstituted phenyl, or unsubstituted biphenyl.

3. The compound of claim 1 wherein B is C=O.
4. The compound of claim 1 wherein B is $CH_2$.
5. The compound of claim 1 wherein B is CHOH.
6. The compound of claim 1 wherein B is CHCl.
7. The compound of claim 1 wherein B is CHF.
8. The compound of claim 1 wherein B is CHBr.
9. The compound of claim 1 wherein B is CHCN.

10. The compound according to claim 1 wherein G is OH.

11. The compound according to claim 1 wherein G is OH.

12. The compound of claim 1 wherein D has a chloro substituent.

13. The compound of claim 12 wherein D has two chloro substituents.

14. The compound of claim 12 wherein D has a hydroxymethyl substituent.

15. The compound of claim 1 wherein a substituent consists of up to 4 carbon atoms, up to 2 oxygen atoms, up to 1 chlorine atoms, and up to 10 hydrogen atoms.

16. The compound of claim 15 wherein each substituent is independently methyl, ethyl, propyl, isopropyl, fluoro, chloro, bromo, hydroxymethyl, or hydroxyethyl.

* * * * *